United States Patent [19]

Ikeda et al.

[11] Patent Number: 5,543,307
[45] Date of Patent: Aug. 6, 1996

[54] METHOD OF MULTIPLYING A VECTOR IN E. COLI HOST

[75] Inventors: Hideo Ikeda, 3-15-13, Nishikoiwa, Edogawa-ku, Tokyo; Toshiyuki Ukita, Yachiyo; Hatsushi Shimizu, Tsukuba, all of Japan

[73] Assignee: Hideo Ikeda, Tokyo, Japan

[21] Appl. No.: 306,911

[22] Filed: Sep. 16, 1994

[30] Foreign Application Priority Data

Mar. 16, 1994 [JP] Japan .................................... 6-045903

[51] Int. Cl.⁶ .......................... C12N 15/68; C12N 15/20; C12N 15/03; C12N 1/20
[52] U.S. Cl. ................................ 435/172.3; 435/252.8; 424/200.1; 935/22; 935/29; 935/42; 935/73
[58] Field of Search ............................ 435/172.3, 252.8; 424/200.1; 935/73, 22, 29, 42

[56] References Cited

PUBLICATIONS

Thoms et al. "Suppression of the UV–Sensitive Phenotype of *E. coli* recF Mutants by recA & (srf) recA(tif) Mutations Requires recJ⁺" J. Bacteriol. 170(8) 3675–3681 1988.

Kusano et al. "Plasmid Mediated Lethality & Plasmid Multimer Formation in an *E. coli* recBC sbcBC Mutant" J Mol. Biol. 209 623–634 1989.

Kolodne et al. "Genetic Recombination of Bacterial Plasmid DNA: Effect of RecF Pathway Mutations of Plasmid Recombination in *E. coli* " J Bacteriol. 163(3) 1060–1066 1985.

Lloyd et al. "Overlapping Functions of recD, recJ & recN Provide Evidence of 3 Epistatic Groups of Genes in *E. coli* Recombination & Repair" Biochimie 73 313–320 1991.

The Japanese Journal of Genetics, vol. 68 No. 5 Oct., 1993 including abstract of presentation (No. 2A15) by Ukita, T. Shimizu, H. and Ikeda, H., presented Sep. 18, 1993.

*Primary Examiner*—Mindy Fleisher
*Assistant Examiner*—Nancy J. Degen
*Attorney, Agent, or Firm*—Fish & Richardson PC

[57] ABSTRACT

A method of retaining or multiplying vector DNA stably in an *Escherichia coli* host comprising the step of culturing the host having both recA and recJ mutations containing said vector.

1 Claim, No Drawings

METHOD OF MULTIPLYING A VECTOR IN E. COLI HOST

FIELD OF THE INVENTION

This invention relates to a method of retaining or multiplying a vector stably using *Escherichia coli* (*E. coli*) host, especially relates to a method of retaining or multiplying a vector using *E. coli* host having both recA and recJ mutations.

BACKGROUND OF THE INVENTION

So far, in the case of retaining or multiplying a vector DNA in *E. coli*, there occurs a problem that the vector is not retained or multiplied stably in the host because the vector DNA, especially the exogenous DNA, recombines and the structure of DNA changes. Therefore, recA mutant in which homologous recombination is drastically suppressed is often used for the host to retain a vector DNA or to express a foreign DNA. But in recA mutant host, nonhomologous recombination is not suppressed because nonhomologous recombination does not require RecA protein.

SUMMARY OF THE INVENTION

The aim of this invention is the remarkable suppression of the recombination of vector in a host and stable retaining or multiplication of vector DNA by suppressing both homologous and nonhomologous recombination in a host.

DETAILED DESCRIPTION OF THE INVENTION

This invention relates to a method of stable retaining or multiplying of a vector DNA in *E. coli* host using host in which the recombination of a vector DNA is remarkably suppressed and the vector DNA is stably retained or multiplied.

RecA gene and recJ gene are known as genes having roles in homologous recombination in *E. coli*. The characteristic of this invention is to use a recA/recJ double mutant strain of *E. coli* as a host for a vector DNA. In said strain, homologous recombination is remarkably suppressed because recA gene which is essential for the homologous recombination is inactivated. Also it was unexpectedly found that nonhomologous recombination was also remarkably suppressed in said recA/recJ double mutant strain. According to the above finding, it was probed that total rate of homologous and nonhomologous recombination is remarkably suppressed in recA/recJ double mutant strain. In addition, it was demonstrated that recA/recJ double mutant strain grows as well in the medium although it carries double mutation. Therefore, it was probed that said recA/recJ double mutant strain is sufficiently useful industrially as a host which is used for retaining or multiplying a vector DNA and if necessary obtaining expression product of a gene.

Principally any strain which carries recA/recJ double mutation can be used as a host of this invention, and, for example, R594 (Virology, 27, p.329 (1965)), C600 (Genetics, 39, p.440 (1954)), or NM538 (J. Mol. Biol., 170, p.827 (1983)) which carries recA/recJ double mutation can be used.

Usual method such as P1 transduction (Tanpakushitu-Kakusan-Kouso, extra number, "Experimental Method for Bacteria/Phage", p.71–72, Kyouritu Syuppann) is used to introduce recA mutation and recJ mutation to each strain. Because the efficiency of transduction is reduced in recA host, it is desirable to introduce recA mutation after the introduction of recJ mutation.

Plasmid vector and phage vector are available for this invention, for example, pUC series plasmid and pBR series plasmid as plasmid vectors, EMBL series phage and λgt series phage as phage vectors are used. Host-vector system of this invention is especially effective for the multiplication of a vector which contains long foreign DNA such as P1 vector or cosmid vector. This invention is applicable for both cloning vector and expression vector. In the case of expression vector, structural gene can be expressed in a host and expression product can be obtained if the structural gene is connected downstream from the promoter.

The host transformed by a vector can be cultured according to the conventional method. Any medium in which *E. coli* can grow can be used, and, for example, L medium, LB medium and SOB medium can be used. It is desirable to incubate *E. coli* on shaking at 25° C.–40° C., and pH 5–9.

The vector can be recovered from the cultured transformed host according to the conventional method. For example, alkaline method or boiling method can be used for plasmid vector (Molecular Cloning second version, J. Sambrook et al., Cold Spring Harbor Laboratory Press (1989), 1.21–1.52) and phage vector can be recovered from phage lysate (Molecular Cloning second version, J. Sambrook et al., Cold Spring Harbor Laboratory Press (1989), 2.60–2.80).

Expression of the structural gene in the transformed *E. coli* which retains a expression vector and collection of expression product case accomplished using the conventional method (Molecular Cloning second version, J. Sambrook et al., Cold Spring Harbor Laboratory Press (1989), Section 17 "Expression of Cloned Genes in *Escherichia coli*").

According to this invention, it became possible that the frequency of the recombination in host is decreased remarkably and vector DNA is stably retained or multiplied in *E. coli* host.

Preferred embodiments concerning this invention are shown as follows, and it is obvious that the scope of this invention is not limited to the preferred embodiments. It is needless to say that the frequency of the homologous recombination is also drastically decreased in said host which carries recA mutation, though said working example only demonstrates experimentally that the frequency of the nonhomologous recombination is decreased in *E. coli* which carries recA/recJ double mutation.

DESCRIPTION OF THE PREFERRED EMBODIMENTS

EXAMPLE 1

System for the detection of nonhomologous recombination

When lysogenyzed λ phage is excised through the phage induction, phage DNA is normally excised through site-specific recombination using art sites which exist at the both end of prophage. But the excision of λ phage through nonhomologous recombination using the sites other than art site occurs at very low frequency. As a result of this nonhomologous recombination, transducing phage named "λ gal" or "λ bio" is formed which contains gal gene or bio gene of *E. coli* in its genome. phage can not grow on P2 lysogen and this characteristics is called as "Spi" (abbreviation of "sensitive to P2 interference"). But λ red —γ— can grow in P2 lysogen exceptionally (λSpi⁻).

The genome structure of λ Spi⁻ phage was examined which was formed through the induction in various condition of wild type strain in which A phage is lysogenyzed using PCR method, and it was demonstrated that 82 strains of 84 strains contain *E. coli* bio gene in its phage genome. Therefore, the frequency of the formation of λ Spi⁻ phage was examined and adopted as an index of the frequency of the occurrence of nonhomologous recombination instead of examining the frequency of the formation of λ bio phage. This frequency measuring method by the detection of λ Spi⁻ phage is suffered from little noise and highly reliable.

EXAMPLE 2

Induction by UV irradiation

Lysogen is cultured in $\lambda_{PY}$ medium (10 g Bacto Tryprone, 2.5 g NaCl, 1 g Yeast Extract, 1.5 g $Na_2HPO_4$, 0.18 g $MgSO_4$ in 1 liter of water) overnight. $\lambda_{PY}$ culture was inoculated with 1/100 volume of that overnight culture and incubated at 30° C. until the cell density reached $1.5 \times 10^8$/ml. Two ml of the culture were irradiated with VU of 0.55 mW/cm² for 10 second with stirring in a glass dish with a diameter of 8.5 cm. The medium in the dish was collected and incubated at 42° C. for 15 min with stirring and then incubated at 37° C. for 2 hours with stirring until lysis. Several drops of $CHCl_3$ were added with additional shaking for another 5 minutes followed by the centrifuge at 3000 rpm for 15 min. The supernatant was collected and diluted with M9 medium and cultured overnight with 0.1 ml of the overnight culture of indicator *E. coli* (Ymel) and λ top medium (10 g Polypeptone, 2.5 g NaCl, 4 g Agar in 1 liter of water) on λ plate (10 g Polypeptone, 2.5 g NaCl, 12 g Agar in 1 liter of water) and plaques formed were counted.

EXAMPLE 3

Measurement of the number of λ Spi⁻ phages $2 \times 10^7$ of phage were cultured with 0.1 ml of overnight culture of P2 lysogen *E. coli* (WL95 (P2):metB supE supF $hsdR_k$ tonA trpR (P2)) and 2.5 ml of λ top medium on λ tripticase plate (10 g of BBL tripticase peptone (Becton Dickinson), 2.5 g of NaCl, 10 g of agar in 1 liter of water) and plaques formed were counted.

EXAMPLE 4

Measurement of the frequency of the formation of λ Spi⁻ phage

The ratio of the λ Spi⁻ phage number in 0.1 ml culture (measured in example 3) against the total phage number in 0.1 ml culture (measured in example 2) is calculated and regarded as the frequency of λ Spi⁻ phage formation.

EXAMPLE 5

Measurement of the frequency of the formation of λ Spi⁻ phage in wild type or mutant hosts The frequency of the formation of λ Spi⁻ phage in wild type host, recA mutant host, recJ mutant host or recA/recJ double mutant host is shown in Table 1.

TABLE 1

| MUTANT | WILD TYPE | recA– | recJ– | recA–/recJ– |
|---|---|---|---|---|
| THE FREQUENCY THE FORMATION OF Spi– PHAGE | $7.9 \times 10^{-7}$ | $5.8 \times 10^{-7}$ | $1.2 \times 10^{-7}$ | $3.4 \times 10^{-8}$ |

As shown in Table 1, the frequency of λ Spi⁻ phage formation in recJ mutant was decreased by about ⅐ compared with wild type host. Therefore, it was proved that the frequency of the nonhomologous recombination was decreased in recJ mutant host compared with wild type host. And as shown in Table 1, the frequency of the λ Spi⁻ phage formation in recA/recJ double mutant host was decreased by about ¼ compared with recJ mutant host, that is to say, the frequency of λ Spi⁻ phage formation in recA/recJ double mutant was decreased by about ¹⁄₂₅ compared with recJ mutant host. Therefore, it was proved that the frequency of the nonhomologous recombination was drastically decreased in recA/recJ double mutant host compared with wild type host.

EXAMPLE 6

Measurement of growth rate of wild type host and mutant host

Wild type of R594 strain (Virology, 27, p.329 (1965)), recA mutant of R594, rec J mutant of R594 or recA/recJ double mutant of R594 was incubated in $\lambda_{PY}$ medium at 37° C. Doubling time in the log-phase was measured. The results are shown in Table 2.

TABLE 2

| MUTANT | WILD TYPE | recA– | recJ– | recA–/recJ– |
|---|---|---|---|---|
| DOUBLING TIME (min) | 21.3 | 32.8 | 23.6 | 27.4 |

As shown in Table 2, the growth rate of these strains were almost the same.

We claim:

1. A method of retaining or multiplying vector DNA stably in an *Escherichia coli* host comprising a step of culturing said host in which non-homologous recombination is suppressed by having both recA and recJ mutations, and which contains said vector DNA.

* * * * *